United States Patent [19]
Scarfone et al.

[11] Patent Number: 5,906,594
[45] Date of Patent: May 25, 1999

[54] ENDOSCOPIC INFUSION NEEDLE HAVING DUAL DISTAL STOPS

[75] Inventors: Frank A. Scarfone, Miramar; Joel F. Giurtino, Miami, both of Fla.

[73] Assignee: Symbiosis Corporation, Miami, Fla.

[21] Appl. No.: 08/778,243

[22] Filed: Jan. 8, 1997

[51] Int. Cl.$^6$ .................................................. A61M 5/178
[52] U.S. Cl. ........................... 604/165; 604/164; 604/264
[58] Field of Search .................................... 604/117, 164, 604/165, 158, 159, 264

[56] References Cited

U.S. PATENT DOCUMENTS

| | | | |
|---|---|---|---|
| 3,530,785 | 9/1970 | Peters et al. | 604/117 X |
| 3,774,604 | 11/1973 | Danielson . | |
| 4,373,526 | 2/1983 | Kling | 604/117 |
| 4,627,841 | 12/1986 | Dorr | 604/158 |
| 4,988,339 | 1/1991 | Vadher | 604/117 X |
| 5,141,496 | 8/1992 | Dalto et al. | 604/117 |
| 5,330,501 | 7/1994 | Tovey et al. | 604/164 X |
| 5,352,206 | 10/1994 | Cushieri et al. | 604/158 X |
| 5,356,389 | 10/1994 | Willing | 604/164 |
| 5,425,718 | 6/1995 | Tay et al. | 604/158 X |
| 5,520,654 | 5/1996 | Wahlberg | 604/164 |
| 5,669,885 | 9/1997 | Smith | 604/164 X |
| 5,672,158 | 9/1997 | Okada et al. | 604/165 X |

OTHER PUBLICATIONS

Directions for use for Injection Gold Probe™ Bipolar Hemostasis Catheter by Microvasive®, Boston Scientific Corporation, Oct. 1994.

*Primary Examiner*—Ronald Stright, Jr.
*Attorney, Agent, or Firm*—Finnegan, Henderson, Farabow, Garrett & Dunner, L.L.P.

[57] ABSTRACT

An endoscopic infusion needle device includes a catheter within which an injection tube having a distal injection needle is slideably disposed. A proximal actuating handle is coupled to the proximal ends of the catheter and the injection tube, and a distal stopping structure is provided on distal portions of the catheter and the injection tube. In one embodiment, the stopping structures include a rigid elongate skeletal structure occupying a portion of the annular space between the tube and the catheter, and an annular band on the tube which resides within the skeletal structure. The skeletal structure fits tightly within the cannula, allows irrigation fluid to pass through the annular space between the tube and the catheter to exit the distal end of the catheter, prevents the annular band from escaping through the proximal end or the distal end of the skeletal structure, and maintains the tube in substantial axial alignment with the catheter. The annular band is located such that when the tube is moved proximally, the distal end of the injection needle is safely housed within the skeletal structure when the annular band is stopped by the skeletal structure; and, when the tube is moved distally, the distal end of the needle extends approximately 4–6 mm beyond the distal end of the skeletal structure when the annular band is stopped by the skeletal structure.

21 Claims, 5 Drawing Sheets

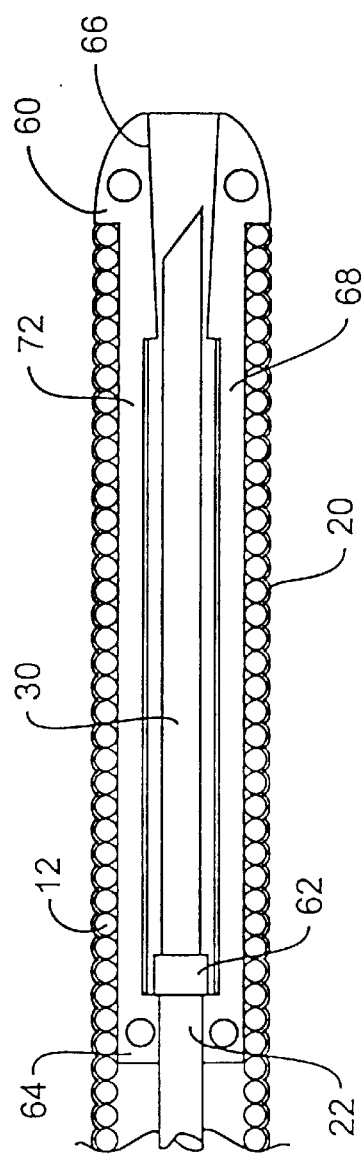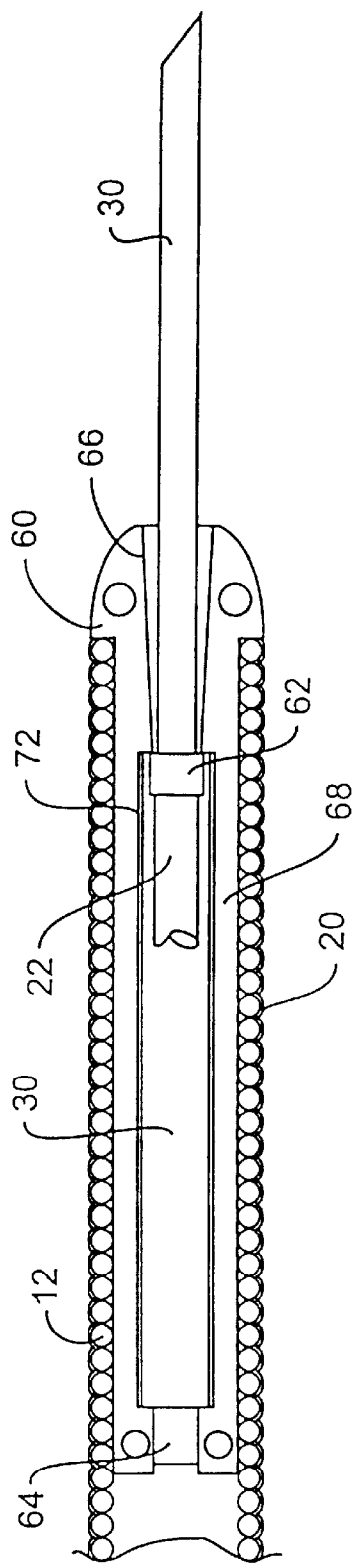

ENDOSCOPIC INFUSION NEEDLE HAVING DUAL DISTAL STOPS

BACKGROUND OF THE INVENTION

1. Field of the Invention

The invention relates to endoscopic medical devices. More particularly, the invention relates to an endoscopic infusion device having a needle which is movable within an outer tube from a first position to a second position.

2. State of the Art

Endoscopic infusion needle devices are used in the treatment of various digestive disorders to control bleeding or potential bleeding lesions in the esophagus, stomach, duodenum, and colon. The state of the art devices include a relatively long catheter, typically having an overall length of about 200 cm, within which an inner injection tube having a distal injection needle is slideably disposed. A proximal actuating handle is coupled to the catheter and the injection tube for moving one relative to the other. Fluid access to the injection tube is typically provided via a luer connector on the handle. In addition, a second luer connector is usually provided on the handle for introducing a saline irrigant into the annular space between the catheter and the injection tube.

Endoscopic infusion needle devices are typically delivered to an injection site through the lumen of an endoscope. In order to protect the lumen of the endoscope from damage, the handle of the infusion needle device is manipulated to withdraw the distal injection needle into the lumen of the catheter before inserting the device into the endoscope. This is important to prevent exposure of the sharp point of the injection needle as the device is moved through the lumen of the endoscope. When the distal end of the infusion needle device is located at the injection site, its handle is again manipulated to move the injection needle distally out of the lumen of the catheter. When advanced to the most distal position, the exposed portion of the injection needle should be approximately 4–6 mm in length. The injection procedure is often preceded by washing the site with saline in order to clear the field of view before piercing the injection site with the needle. The saline wash is delivered via the annular space between the catheter and the injection tube. After the injection site has been pierced, a sclerosing agent or vasoconstrictor composition is delivered through the injection tube and the needle into the injection site. The procedure may be performed at several injection sites before the injection needle device is removed from the endoscope. Between injections, however, the needle is withdrawn into the catheter to prevent inadvertent punctures or needle pricks.

The state of the art endoscopic infusion needle devices all suffer from similar design problems which are related to the movement of the needle into and out of the catheter. For example, it is difficult to assure that the injection needle will remain within the catheter when it is withdrawn, or to assure that the injection needle will not puncture the wall of the catheter during movement of the device through the endoscope. The reason for these problems is related to the dimensions of the device and the often tortuous path provided by the lumen of the endoscope. As mentioned above, the desired relative movement of the needle and the catheter is only on the order of 10 mm, whereas the overall length of the device is on the order of two hundred times that amount. Thus, the movement of the proximal ends of the catheter and the injection tube by an amount on the order of 10 mm cannot assure that the distal ends of the catheter and the injection tube will move exactly the same amount without requiring exacting tolerances. This issue is exacerbated by the tortuous path taken through the endoscope by the device. This tortuous path also causes the injection needle to be deflected relative to the axis of the catheter such that the sharp point of the needle touches the inner wall of the catheter. As the device is moved through the endoscope, it is thereby possible for the injection needle to puncture the catheter wall, rendering the device inoperative, and possibly damaging the lumen of the endoscope.

SUMMARY OF THE INVENTION

It is therefore an object of the invention to provide an endoscopic infusion needle device which assures that the distal ends of the catheter and the injection tube can be moved relative to each other between two well-defined positions.

It is also an object of the invention to provide an endoscopic infusion needle device which assures that the sharp end of the injection needle will not contact the inner wall of the catheter.

It is another object of the invention to provide an endoscopic infusion needle device which is inexpensive to manufacture.

It is still another object of the invention to provide an endoscopic infusion needle device which does not require exacting tolerances to assure the well-defined positions of the catheter and the injection tube.

In accord with these objects which will be discussed in detail below, the endoscopic infusion needle device of the present invention includes a relatively long catheter within which an inner injection tube having a distal injection needle is slideably disposed. A proximal actuating handle is coupled to the proximal ends of the catheter and the injection tube for moving one relative to the other, and distal stopping structures are provided on distal portions of the catheter and the injection tube. Fluid access to the injection tube is provided via a luer connector on the handle, and a second luer connector is provided on the handle for introducing a saline irrigant into the annular space between the catheter and the injection tube. According to one embodiment of the invention, the distal stopping structures include a rigid elongate skeletal structure which is inserted into the distal end of the catheter and which occupies a portion of the annular space between the injection tube and the catheter wall, and an annular band on a portion of the injection tube which resides within the skeletal structure. The skeletal structure is dimensioned such that it fits tightly within the cannula, allows irrigation fluid to pass through the annular space between the injection tube and the catheter and to exit the distal end of the catheter, and prevents the annular band from escaping through the proximal end or the distal end of the skeletal structure. In addition, the skeletal structure is dimensioned to maintain the injection needle in substantial axial alignment with the catheter. The annular band is located on the injection tube such that when the injection tube is moved proximally relative to the catheter, the distal end of the injection needle is safely housed within the skeletal structure when the annular band is stopped by the skeletal structure; and, when the injection tube is moved distally relative to the catheter, the distal end of the injection needle extends approximately 4–6 mm beyond the distal end of the skeletal structure when the annular band is stopped by the skeletal structure. According to other embodiments of the invention, two annular bands are provided on the injection tube and one or more stopping structures are provided within the cannula.

The distal stopping structure according to the invention provides a positive well-defined proximal stopping location and a positive well-defined distal stopping location for the injection needle. In addition, several embodiments of the stopping structure provide an axial alignment for the injection needle which prevents the needle from puncturing the catheter.

Additional objects and advantages of the invention will become apparent to those skilled in the art upon reference to the detailed description taken in conjunction with the provided figures.

BRIEF DESCRIPTION OF THE DRAWINGS

FIG. 2 is an enlarged broken side elevation view in partial section of the distal end of the infusion needle device of FIG. 1 in a retracted position;

FIG. 3 is an enlarged broken side elevation view in partial section of the distal end of the infusion needle device of FIG. 1 in an extended position;

DETAILED DESCRIPTION OF THE PREFERRED EMBODIMENTS

Figure 1:
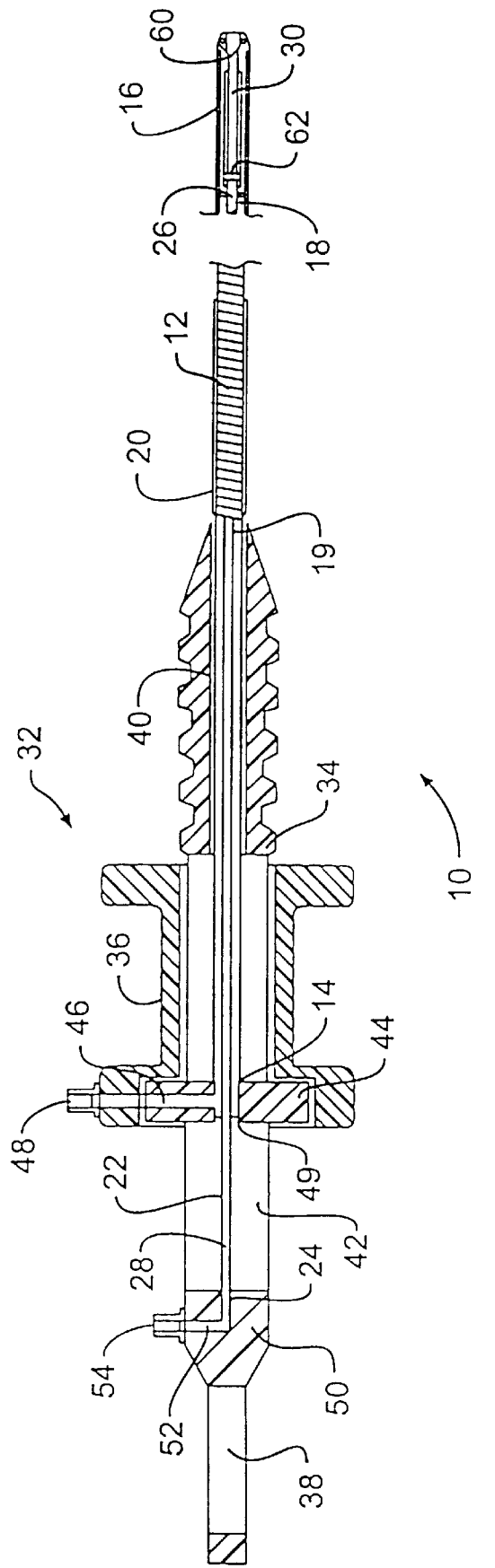
FIG. 1 is a broken side elevation view in partial section of a first embodiment of an endoscopic infusion needle device according to the invention.

Referring now to FIGS. 1 through 3, an endoscopic infusion needle device 10 according to the invention includes a relatively long flexible catheter 12 having a proximal end 14, a distal end 16, and defining a lumen 18. As shown, the catheter 12 is a steel coil covered with a PTFE, FEP or polyolefin sheath 20 along substantially its entire length. A flexible, preferably metallic injection tube 22 having a proximal end 24, a distal end 26, and defining an injection lumen 28 is slideably disposed within the lumen 18 of the catheter 12 and defines an annular space 19 between the tube 22 and the catheter 12. The distal end 26 of the injection tube 22 is provided with an injection needle 30 which is in fluid communication with the injection lumen 28 of the injection tube 22.

The proximal ends 14, 24 of the catheter and the injection tube are coupled to an actuation handle 32 which includes a central shaft 34 and a displaceable spool 36. The proximal end of the shaft 34 is provided with a thumb ring 38 and a longitudinal bore 40 is provided at the distal end of the shaft 34. A longitudinal slot 42 extends from the proximal end of bore 40 to a point distal of the thumb ring 38. The displaceable spool 36 is provided with a cross member 44 which passes through the slot 42 in the central shaft 34. The proximal end 14 of the catheter 12 is coupled to the cross member 44 which is provided with a fluid conduit 46 terminating in a luer connector 48. The fluid conduit 46 provides a fluid path from the luer 48 to the lumen 18 of the catheter 12. An O-ring 49 in the cross member 44, proximal of the fluid conduit 46, seals the annulus between the catheter 12 and the injection tube 22. The proximal end 24 of the injection tube 22 is coupled to a proximal portion 50 of the shaft 34 which is intermediate of the thumb ring 38 and the slot 42. The portion 50 is provided with a fluid conduit 52 terminating in a luer connector 54 which provides a fluid path from the luer to the injection lumen 28 of the injection tube 22.

From the foregoing, those skilled in the art will appreciate that when the thumb ring 38 and the spool 36 are moved toward each other, the injection tube 22 will be axially displaced relative to the catheter 12 such that the needle 30 extends out of the distal end of the catheter 12 as shown in FIG. 3. When the thumb ring 38 and the spool 36 are moved away from each other, the injection tube 22 will be axially displaced relative to the catheter 12 such that the needle 30 is drawn into the distal end of the catheter 12 as shown in FIGS. 1 and 2. Furthermore, it will be appreciated that a source of irrigating fluid (not shown) may be coupled to the luer 48 and the irrigating fluid will be directed through the lumen 18 of the catheter in the annular space defined by the injection tube 22 and the catheter 12 and will exit from the distal end of the catheter. In addition, it will be appreciated that a source of injection fluid (not shown) may be coupled to the luer 54 and the injection fluid will be directed through the lumen 28 of the injection tube and will exit from the distal end of the injection needle 30.

According to a first embodiment of the invention, a distal portion of the catheter 12 is provided with a rigid elongate skeletal structure 60 which is inserted in the distal end of the catheter 12 and which occupies a portion of the annular space between the injection tube 22 and the catheter 12. A distal portion of the injection tube 22 or a proximal portion of the injection needle 30 is provided with an annular band 62 which resides within the skeletal structure 60. As described in more detail below with reference to FIGS. 4 and 5, the skeletal structure 60 is dimensioned such that it fits tightly within the catheter 12, allows irrigation fluid to pass through the annular space between the injection tube 22 and the catheter 12 and to exit the distal end of the catheter, and prevents the annular band 62 from escaping through the proximal end or the distal end of the skeletal structure 60. In addition, the skeletal structure is dimensioned to maintain the injection tube 22 and the needle 30 in substantial axial alignment with the catheter 12. The annular band 62 is located such that when the injection tube is moved proximally relative to the catheter, as shown in FIG. 2, the distal end of the injection needle 30 is safely housed within the skeletal structure when the annular band 62 is stopped by the skeletal structure. When the injection tube 22 is moved distally relative to the catheter 12, as shown in FIG. 3, the distal end of the injection needle extends approximately 4–6 mm beyond the distal end of the skeletal structure 60 when the annular band 62 is stopped by the skeletal structure.

Figure 4:
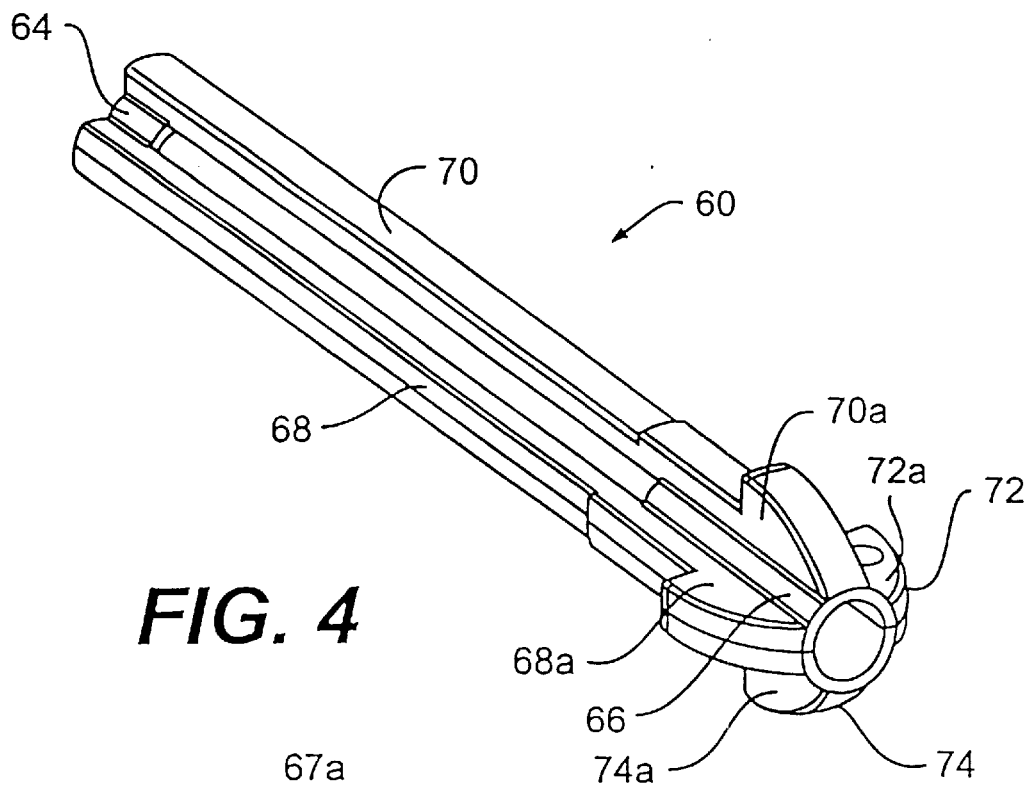
FIG. 4 is a perspective view of the coil stiffening and needle stopping structure of the infusion needle device of FIGS. 1–3.
Figure 5:
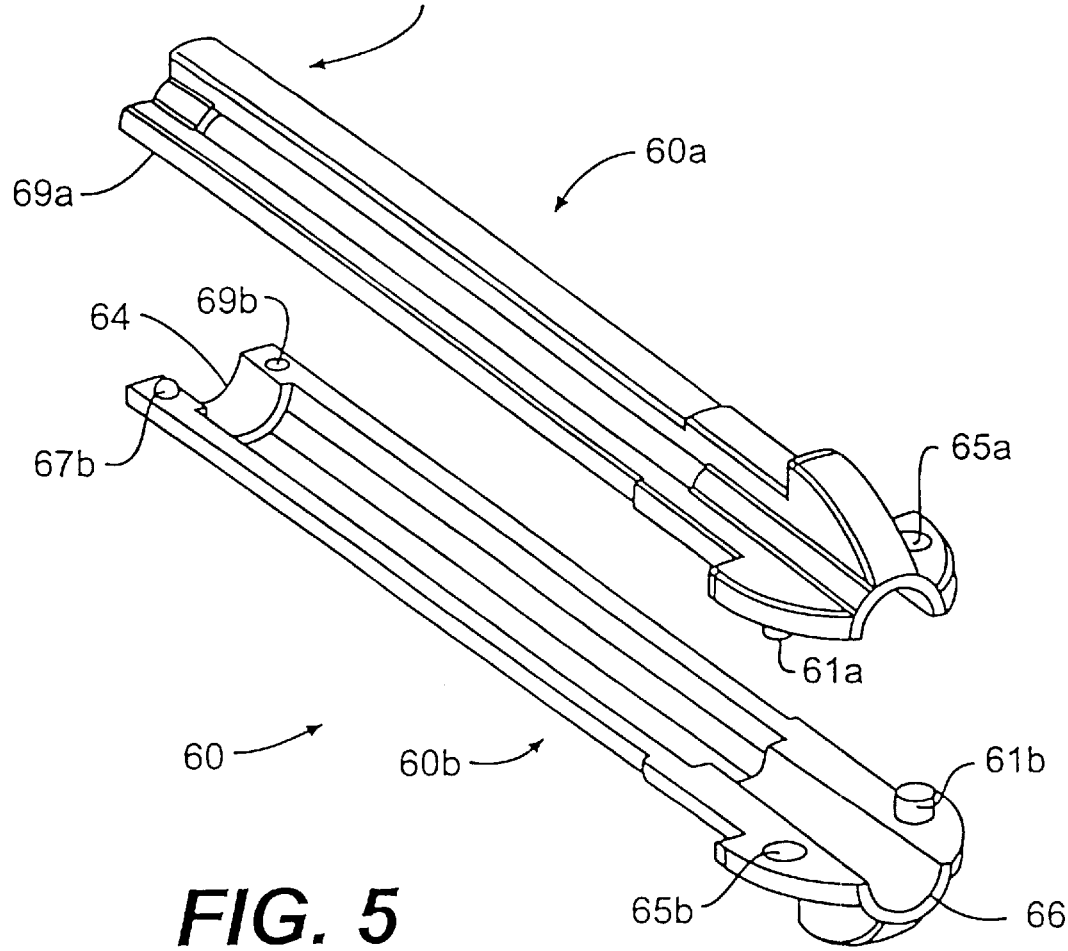
FIG. 5 is an exploded perspective view of the coil stiffening and needle stopping structure of the infusion needle device of FIGS. 1–3.

Turning now to FIGS. 4 and 5, according to a presently preferred embodiment, the skeletal structure 60 includes a proximal cylindrical member 64, a distal cylindrical member 66, and four longitudinal outer struts or splines 68, 70, 72, 74 which connect the cylindrical members 64, 66. The struts are arranged at regular intervals around the outer surfaces of the cylindrical members and are intended to center the cylindrical members 64, 66 while providing a fluid flow path. The struts 68, 70, 72, 74 are preferably provided with stepped distal portions 68a, 70a, 72a, 74a which rise abruptly and form a seat for receiving the distal end of the catheter 12 and then curve inward to form a smooth distal end. According to the presently preferred embodiment, the skeletal structure 60 is formed from two identical members 60a, 60b with mating pegs 61a, 61b, 67a, 67b and holes 65a, 65b, 69a, 69b, and which are bonded together.

Referring once again to FIGS. 2 and 3, and in view of the foregoing, it will be appreciated that the diameter of the proximal cylindrical member 64 of the skeletal structure 60 is large enough to allow free passage of the injection tube 22, but too small to allow the passage of the annular band 62. Similarly, the diameter of the distal cylindrical member 66 is large enough to allow free passage of the injection needle 30, but too small to allow the passage of the annular band 62. According to a presently preferred embodiment, the diameter of the injection tube 22 is approximately 0.028 inches; the diameter of the injection needle is approximately 0.020 inches (25G); and the diameter of the annular band is approximately 0.035 inches. The space between the struts is sufficient to allow passage of irrigant through the distal end of the catheter.

From the foregoing and with reference to FIGS. 1–5, generally, it will be appreciated that the skeletal structure 60 and the annular band 62 provide a positive well-defined proximal stopping location (FIG. 2) and a positive well-defined distal stopping location (FIG. 3) for the injection needle 30. In addition, the skeletal structure provides an axial alignment for the injection needle 30 which prevents the needle from puncturing the catheter 12. While the first embodiment of the invention has been shown in conjunction with a coated steel coil catheter, it will be appreciated that other types of catheters could be used, such as flexible plastic catheters.

Figure 6:
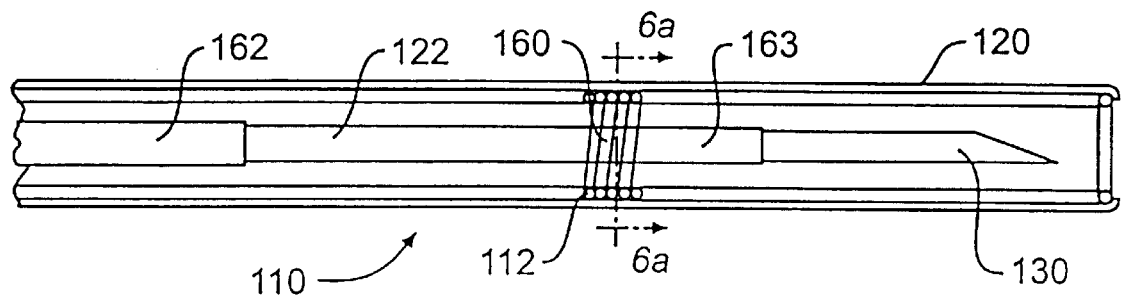
FIG. 6 is an enlarged broken side elevation view in partial section of the distal end of a second embodiment of an infusion needle device according to the invention.
Figure 6A:
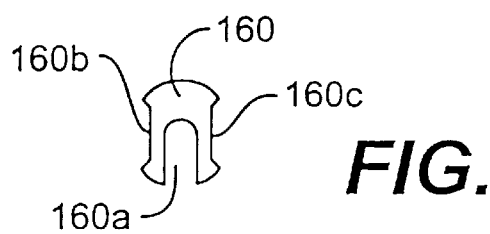
FIG. 6a is a cross sectional view taken along line 6A—6A in FIG. 6.

FIGS. 6 and 6a show a second embodiment 110 of the invention where parts similar to the first embodiment are indicated by similar reference numerals increased by 100. According to the second embodiment, the distal end of the injection tube 122 is provided with two spaced apart annular bands 162, 163. At least one stopping washer 160 is placed between adjacent coils of the catheter 112 such that the washer(s) reside between the annular bands 162, 163. As seen best in FIG. 6a, the stopping washer 160 is substantially disk shaped with a radial cutout 160a and two side cutouts 160b, 160c. When the washer 160 is inserted radially in between adjacent coils of the catheter 112, the radial cutout 160a receives the injection tube 122 and the side cutouts 160b, 160c allow the passage of irrigant through the distal end of the catheter 112. It will be appreciated that the dimensions of the radial cutout 160a are such that the washer prevents distal passage of the proximal annular band 162 and prevents proximal passage of the distal annular band 163. Preferably two washers are used with their radial cutouts oriented in opposite directions to provide an axial alignment of the injection tube 122 with the catheter 112. From the foregoing, those skilled in the art will appreciate that the washer(s) 160 and the bands 162, 163 cooperate to provide a positive well-defined proximal stopping location for the needle 130 wherein the needle is shrouded by the catheter 112 and a positive well-defined distal stopping location where the injection needle 130 extends approximately 4–6 mm out of the catheter 112.

Figure 7:
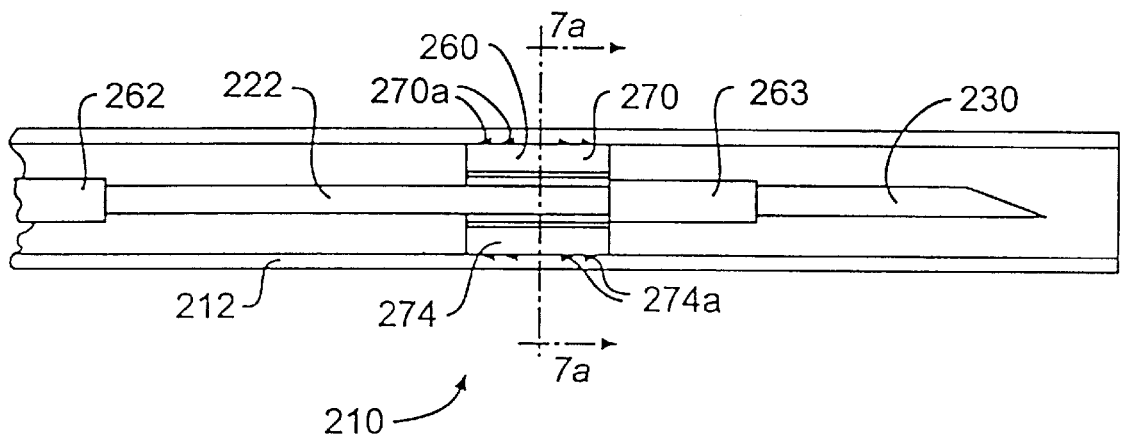
FIG. 7 is an enlarged broken side elevation view in partial section of the distal end of a third embodiment of an infusion needle device according to the invention.
Figure 7A:
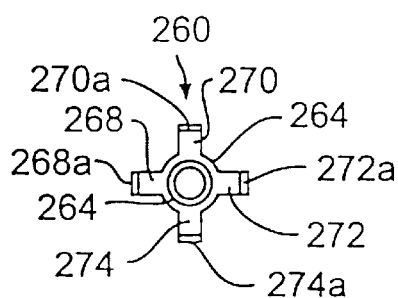
FIG. 7a is a cross sectional view taken along line 7A—7A in FIG. 7.

FIGS. 7 and 7a show a third embodiment 210 of the invention where parts similar to the first embodiment are indicated by similar reference numerals increased by 200. The third embodiment of the invention is preferably used with a plastic catheter. According to the third embodiment, the distal end of the injection tube 222 is provided with two spaced apart annular bands 262, 263. A strutted barbed cylindrical stop 260 is pressed into the distal end of the catheter 212 such that the stop resides between the annular bands 262, 263. As seen best in FIG. 7a, the stop 260 has a central cylinder 264 with four outer struts 268, 270, 272, 274. Preferably, each strut is provided with barbs 268a, 270a, 272a, 274a. When the stop 260 is inserted axially into the distal end of the catheter 212, the barbed struts engage the interior of the catheter after several hours of cold setting. Alternatively, the catheter may be dilated with heat before inserting the stop. It will be appreciated that the dimensions of the cylinder 264 are such that it prevents distal passage of the proximal annular band 262 and prevents proximal passage of the distal annular band 263. The struts 268, 270, 272, 274 are dimensioned and arranged to allow free passage of irrigant through the distal end of the catheter. From the foregoing, those skilled in the art will appreciate that the stop 260 and the bands 262, 263 cooperate to provide a positive well-defined proximal stopping location for the needle 230 wherein the needle is shrouded by the catheter 212 and a positive well-defined distal stopping location where the injection needle 230 extends approximately 4–6 mm out of the catheter 212.

Figure 8:
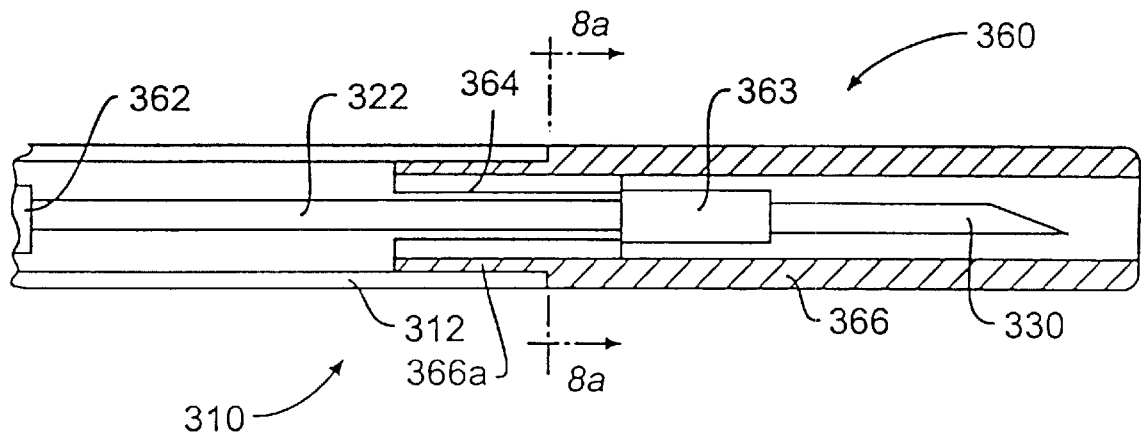
FIG. 8 is an enlarged broken side elevation view in partial section of the distal end of a fourth embodiment of an infusion needle device according to the invention.
Figure 8A:
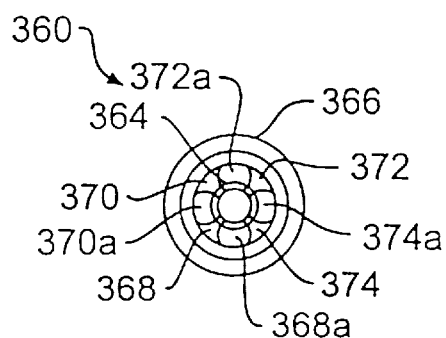
FIG. 8a is a cross sectional view taken along line 8A—8A in FIG. 8.

FIGS. 8 and 8a show a fourth embodiment 310 of the invention where parts similar to the first embodiment are indicated by similar reference numerals increased by 300. The fourth embodiment of the invention is shown with a plastic catheter 312, but may be used with any type of catheter. According to the fourth embodiment, the distal end of the injection tube 322 is provided with two spaced apart annular bands 362, 363 and a distal stopping structure 360 is inserted into the distal end of the catheter 312. The stopping structure has a proximal inner cylinder 364 and an outer cylinder 366 having a reduced diameter proximal portion 366a which fits into the distal end of the catheter 312. The proximal inner cylinder 364 is coupled to the outer cylinder by four radial struts 368, 370, 372, 374 which define four longitudinal fluid paths 368a, 370a, 372a, 374a between the inner cylinder 364 and the outer cylinder 366. The diameter of the inner cylinder 364 is such that it prevents distal passage of the proximal annular band 362 and prevents proximal passage of the distal annular band 363. When used with a plastic catheter, the reduced diameter portion 366a of the outer cylinder is solvent bonded to the catheter. When used with a steel coil catheter, the reduced diameter portion 366a may be provided with outer threads (not shown) to engage the coils of the catheter. The length of the outer cylinder 366 and the location of the bands 362, 364 are chosen so that the inner cylinder and the bands cooperate to provide a positive well-defined proximal stopping location for the needle 330 wherein the needle is shrouded by the outer cylinder 360 and a positive well-defined distal stopping location where the injection needle 330 extends approximately 4–6 mm out of the outer cylinder 360.

There have been described and illustrated herein several embodiments of an endoscopic infusion needle device. While particular embodiments of the invention have been described, it is not intended that the invention be limited thereto, as it is intended that the invention be as broad in scope as the art will allow and that the specification be read likewise. Thus, while particular types of catheters have been disclosed, it will be appreciated that other catheters could be utilized. Also, while several specific distal stopping structures have been shown, it will be recognized that other types of distal stopping structures could be used with similar results obtained. Moreover, while particular configurations have been disclosed in reference to the proximal handle, it will be appreciated that other configurations could be used as well. In addition, while certain structures have been identified as being cylindrical, it will be understood than a substantially cylindrical structure can achieve the same results. Similarly, while one of the stopping structures has been described as an annular band, it will be appreciated that other types of surface structures such as bumps or struts could be used. Furthermore, while the device has been disclosed as having specific dimensions, it will be understood that other dimensions can achieve the same or similar function as disclosed herein.

It will therefore be appreciated by those skilled in the art that yet other modifications could be made to the provided invention without deviating from its spirit and scope as so claimed.

We claim:

1. An endoscopic infusion needle device, comprising:
   a) a catheter having a proximal end, a distal end, and defining a first lumen;
   b) an injection tube having a proximal end, a distal end, and defining a second lumen, said injection tube extending at least partially through said first lumen and defining an annular space between said injection tube and said catheter;
   c) an injection needle coupled to said distal end of said injection tube, said injection needle having an injection lumen in fluid communication with said second lumen;
   d) a proximal actuating means coupled to said proximal end of said catheter and to said proximal end of said injection tube for axially displacing said catheter and said injection tube relative to one another;
   e) injection fluid port means coupled to said second lumen for introducing an injection fluid into said injection lumen;
   f) a first distal stopping structure coupled to a distal portion of said catheter, wherein at least a portion of the first distal stopping structure extends within the catheter lumen; and
   g) a second distal stopping structure coupled to at least one of said injection tube and said injection needle, wherein at least a portion of said second distal stopping structure is moveable with the injection tube and needle within the catheter lumen, and wherein
   said first and second distal stopping structures cooperate with one another to provide a positive well-defined proximal stopping location wherein said injection needle is shrouded by said catheter, and to provide a positive well-defined distal stopping location wherein said injection needle extends out of said catheter.

2. An endoscopic infusion needle device according to claim 1, wherein:
   said first distal stopping structure includes at least one substantially cylindrical member having a plurality of substantially radial exterior struts, said at least one substantially cylindrical member being arranged inside said first lumen such that said struts engage said catheter and at least one of said injection tube and said injection needle passes through said at least one substantially cylindrical member, and
   said second distal stopping structure includes at least one annular structure coupled to one of said injection tube and said injection needle.

3. An endoscopic infusion needle device according to claim 2, wherein:
   said first distal stopping structure includes two substantially cylindrical members having a plurality of substantially radial exterior struts, said two substantially cylindrical members being arranged inside said first lumen such that one of said injection tube and said injection needle passes through said two substantially cylindrical member and said struts engage said catheter, and
   said at least one annular structure resides in between said two substantially cylindrical members.

4. An endoscopic infusion needle device according to claim 3, wherein:
   said two substantially cylindrical members are coupled to each other by a plurality of splines.

5. An endoscopic infusion needle device according to claim 4, wherein:
   said first distal stopping structure extends partially out of said distal end of said catheter.

6. An endoscopic infusion needle device according to claim 5, wherein:
   said first distal stopping structure has a smooth distal end.

7. An endoscopic infusion needle device according to claim 4, wherein:
   said first distal stopping structure is made of two identical pieces.

8. An endoscopic infusion needle device according to claim 1, wherein:
   said second distal stopping structure includes two annular structures, each coupled to one of said injection tube and said injection needle, and
   said first distal stopping structure resides in between said two annular structures.

9. An endoscopic infusion needle device according to claim 8, wherein:
   said first distal stopping structure includes a substantially cylindrical member having a plurality of outer struts.

10. An endoscopic infusion needle device according to claim 9, wherein:
    said struts include outwardly extending barbs.

11. An endoscopic infusion needle device according to claim 9, wherein:
    said struts are arranged substantially radially relative to said substantially cylindrical member.

12. An endoscopic infusion needle device according to claim 8, wherein:
    said first distal stopping structure includes a washer having a radial opening.

13. An endoscopic infusion needle device according to claim 1, further comprising:
    h) irrigation fluid port means coupled to said first lumen for introducing an irrigant into said annular space, wherein
    said first and second distal stopping structures permit said irrigant to flow out of said distal end of said catheter.

14. An endoscopic infusion needle device, comprising:
    a) a catheter having a proximal end, a distal end, and defining a first lumen;
    b) an injection tube having a proximal end, a distal end, and defining a second lumen, said injection tube extending at least partially through said first lumen and defining an annular space between said injection tube and said catheter;
    c) an injection needle coupled to said distal end of said injection tube, said injection needle having an injection lumen in fluid communication with said second lumen;
    d) a proximal actuating means coupled to said proximal end of said catheter and to said proximal end of said injection tube for axially displacing said catheter and said injection tube relative to one another;
    e) injection fluid port means coupled to said second lumen for introducing an injection fluid into said injection lumen;
    f) a first distal stopping structure coupled to a distal portion of said catheter, said first distal stopping structure having a first substantially cylindrical portion extending beyond said distal end of said catheter, wherein at least a portion of the first distal stopping structure extends within the catheter lumen; and g) a second distal stopping structure coupled to at least one of said injection tube and said injection needle, wherein at least a portion of said second distal stopping structure is moveable with the injection tube and needle within the catheter lumen, and wherein said first and second distal stopping structures cooperate with one another to provide a positive well-defined proximal stopping location wherein said injection needle is shrouded by said first substantially cylindrical portion, and to provide a positive well-defined distal stopping location wherein said injection needle extends out of said first substantially cylindrical portion.

15. An endoscopic infusion needle device according to claim 14, wherein:

said first distal stopping structure includes a second substantially cylindrical portion residing within said first substantially cylindrical portion and coupled to said first substantially cylindrical portion by a plurality of struts, one said injection tube and said injection needle extending through said second substantially cylindrical portion.

16. An endoscopic infusion needle device according to claim 15, wherein:

said second distal stopping structure includes at least one annular structure coupled to one of said injection tube and said injection needle.

17. An endoscopic infusion needle device according to claim 15, wherein:

said second distal stopping structure includes two annular structures, each coupled to one of said injection tube and said injection needle, said second substantially cylindrical portion residing in between said two annular structures.

18. An endoscopic infusion needle device, comprising:

a) a catheter having a proximal end, a distal end, and defining a first lumen;

b) an injection tube having a proximal end, a distal end, and defining a second lumen, said injection tube extending at least partially through said first lumen and defining an annular space between said injection tube and said catheter;

c) an injection needle coupled to said distal end of said injection tube, said injection needle having an injection lumen in fluid communication with said second lumen;

d) a proximal actuating means coupled to said proximal end of said catheter and to said proximal end of said injection tube for axially displacing said catheter and said injection tube relative to one another;

e) injection fluid port means coupled to said second lumen for introducing an injection fluid into said injection lumen;

f) a centering structure coupled to a distal portion of said catheter, wherein said centering structure maintains said injection needle in substantial axial alignment with said distal portion of said catheter during movement of said injection needle within said first lumen, wherein said centering structure includes means for limiting a range of motion of said injection needle relative to said catheter between a first position wherein said injection needle is shrouded by said centering structure to a second position wherein said injection needle extends distally beyond said centering structure, and wherein the means for limiting a range of motion includes a first stopping structure attached to a portion of the needle and moveable with said needle within said first lumen of said catheter.

19. An endoscopic needle device according to claim 18, wherein:

said centering structure includes a substantially rigid structure, and wherein said injection needle is shrouded by said substantially rigid structure in said first position, and said injection needle extends distally beyond said substantially rigid structure in said second position.

20. An endoscopic needle device according to claim 19, wherein:

said centering structure further includes a second stopping structure for engaging the first stopping structure attached to the needle in order to provide a positive stop at at least one of said first and second positions.

21. An endoscopic infusion needle device, comprising:

a) a catheter having a proximal end, a distal end, and defining a first lumen;

b) an injection tube having a proximal end, a distal end, and defining a second lumen, said injection tube extending at least partially through said first lumen and defining an annular space between said injection tube and said catheter;

c) an injection needle coupled to said distal end of said injection tube, said injection needle having an injection lumen in fluid communication with said second lumen;

d) a proximal actuating means coupled to said proximal end of said catheter and to said proximal end of said injection tube for axially displacing said catheter and said injection tube relative to one another;

e) a first distal stopping structure including at least one substantially cylindrical member having a plurality of substantially radial exterior struts, wherein said first distal stopping structure is coupled to a distal portion of said catheter and said at least one substantially cylindrical member extends within the first lumen such that said struts engage the catheter and at least one of said injection tube and said injection needle passes through said at least one substantially cylindrical member; and f) a second distal stopping structure including at least one annular structure coupled to at least one of said injection tube and said injection needle, wherein said first and second distal stopping structures cooperate with one another to provide a positive well-defined proximal stopping location wherein said injection needle is shrouded by said catheter, and to provide a positive well-defined distal stopping location wherein said injection needle extends out of said catheter.

* * * * *